United States Patent [19]

Shene et al.

[11] Patent Number: 4,595,019

[45] Date of Patent: Jun. 17, 1986

[54] STONE DISINTEGRATOR

[76] Inventors: William R. Shene, 7 W. Court St., Plattsburgh, N.Y. 12901; Glen Brisson, 22358 Timberlea La., Kildeer, Ill. 60047

[21] Appl. No.: 606,981

[22] Filed: May 4, 1984

[51] Int. Cl.[4] ............................................. A61B 5/05
[52] U.S. Cl. .................................... 128/734; 128/328
[58] Field of Search .......... 128/328, 734, 737, 303.13, 128/908, 303 R, 24 A, 303.14

[56] References Cited

U.S. PATENT DOCUMENTS

| 3,566,233 | 2/1971 | Kahn ................................... 128/734 |
| 3,902,499 | 9/1975 | Shene . |
| 4,114,623 | 9/1978 | Meinke et al. ................. 128/303.14 |
| 4,380,237 | 4/1983 | Newbower ........................ 128/734 |
| 4,416,277 | 11/1983 | Newton et al. ..................... 128/908 |

Primary Examiner—Kyle L. Howell
Assistant Examiner—Daniel Haneiwich

[57] ABSTRACT

An instrument for attacking calculi of a patient by hydraulic impacts formed by electrical discharges in a liquid medium surrounding the calculi by detecting if the discharge end of the lithotrite of the instrument is adjacent to tissue of the patient and detecting by measuring the conductivity of the liquid medium and determining whether the measured conductivity falls within predetermined levels.

9 Claims, 5 Drawing Figures

STONE DISINTEGRATOR

BACKGROUND OF INVENTION (a) Field of the Invention

The invention relates to improvements to an instrument for attacking calculi in a liquid medium surrounding the calculi which improvement comprises means for detecting whether the lithotrite of the instrument is abutting tissue of the patient. More specifically, the invention relates to such an instrument wherein the means for detecting comprises means for sensing the conductivity of the liquid medium.

(b) Description of Prior Art

Instruments of the above-described type, for example, instruments for disintegrating stones in a human patient, are known in the art as illustrated in, for example, U.S. Pat. No. 3,902,499, Shene, issued Sept. 2, 1975. The known instruments suffer the disadvantage of not having any indication when the lithotrite may be touching the tissue of a patient. As will be apparent, if the lithotrite is in such a position when discharged, then the patient can be hurt.

SUMMARY OF INVENTION

It is therefore an object of the invention to provide improvements in instruments for attacking calculi in a liquid medium surrounding the calculi to overcome the disadvantages of prior art such instruments.

It is a further object of the invention to provide such an improved instrument which includes a means for determining when the lithotrite of the instrument is abutting the tissue of the human patient.

It is an even more specific object of the invention to provide such an improved instrument with such means for detecting wherein the means for detecting comprises means for sensing the conductivity of the liquid medium.

In accordance with the invention there is provided the improvement in an instrument as abovedescribed which includes a means for detecting if the discharge end of the lithotrite of the instrument is adjacent to tissue of a patient.

In accordance with an embodiment of the invention, the means for detecting comprises means for measuring the conductivity of the liquid medium surrounding the calculi. Means may be provided for determining whether the measured conductivity falls within predetermined levels.

BRIEF DESCRIPTION OF DRAWINGS

The invention will be better understood by an examination of the following description, together with the accompanying drawings, in which.

DESCRIPTION OF PREFERRED EMBODIMENTS

Figure 1:
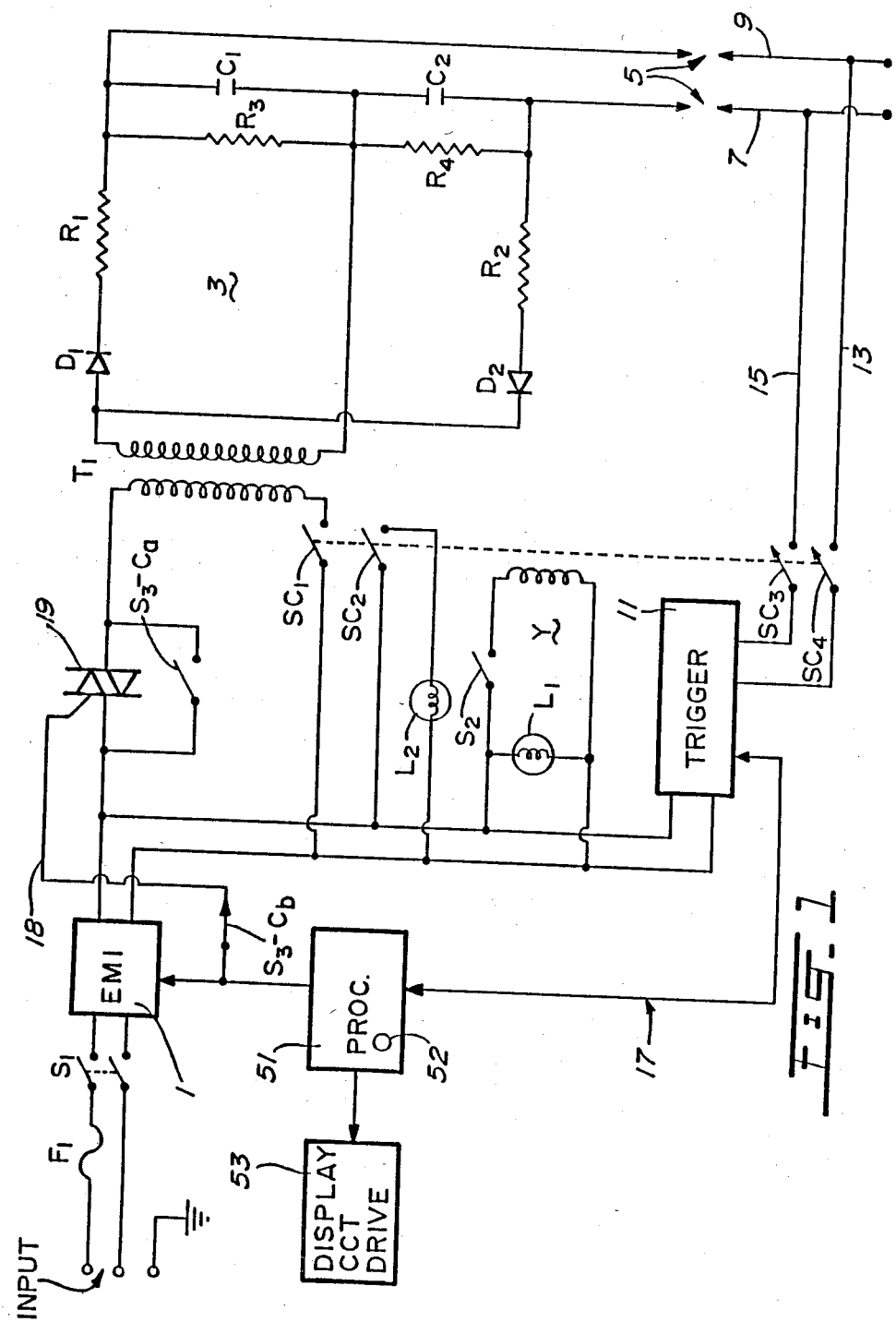
FIG. 1 is a circuit diagram of the improved instrument.

Referring first to FIG. 1, the arrangement comprises an ON/OFF switch, illustrated schematically at S1, and a foot pedal switch, illustrated schematically at S2. A fuse F1 is provided for safety reasons as is well known in the art. An EMI filter 1 is also provided at the input. A transformer T1 has its primary connected to the input and its secondary connected to pulse forming network 3 which includes diodes D1, D2, and resistors R1, R2, R3 and R4. The output of the pulse forming network is fed to discharge capacitors C1 and C2, and the discharge capacitors are connected to discharge through a switching arrangement, illustrated in FIG. 1 as spark gap arrangement 5. In the U.S. Pat. No. 3,902,499 abovementioned, the capacitor is discharged through a solid-state switch arrangement.

The input is also fed through a relay Y through a foot pedal switch illustrated schematically at S2. In parallel with the relay Y is a lamp L1 which indicates that the ON/OFF switch S1 has been turned on.

The input is also fed through a foot pedal indicator lamp, illustrated schematically at L2. L2 is in circuit with a contact SC2 of relay Y. Contact SC1 of relay Y is in series with the primary of the transformer T1.

Figure 3:
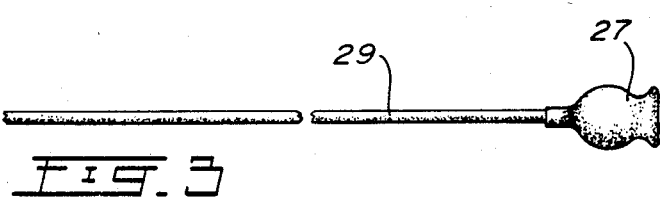
FIG. 3 illustrates a lithotrite and cable.
Figure 4A:
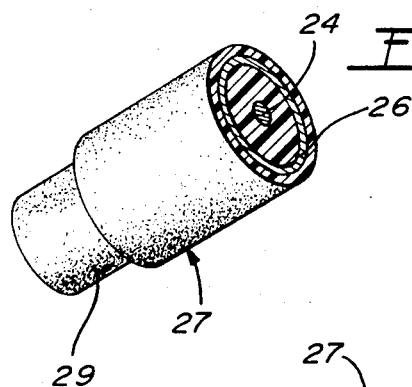
FIGS. 4a and 4b illustrate the free ends of two lithotrites.
Figure 4B:
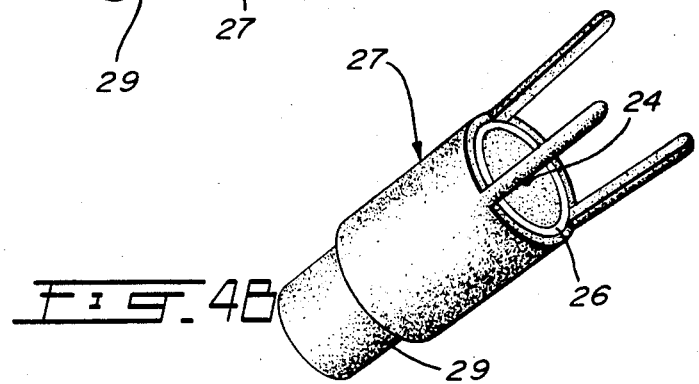

As can be seen, leads 7 and 9 connected, respectively, to capacitors C1 and C2, are connected to the center conductor 24 and outer conductor sleeve 26 of a lithotrite illustrated at 27 in FIGS. 3, 4a and 4b. In FIG. 3, cable 29 constitutes the cable which will carry the leads including leads 7 and 9.

The above-described portion of the circuit, or various modifications thereof, are already well known in the art.

In accordance with the present invention, there is provided a sensing and trigger means 11. The sensing and trigger means is connected, by leads 13 and 15, to leads 9 and 7 respectively to thereby be connected to the lithotrite 27. Lead 15 is connected to 11 through contact SC3 of the relay Y while lead 13 is connected to 11 via contact SC4 of relay Y.

Extension 18 of lead 17 of sensing and trigger means 11 is connected to a control terminal of an electronic switch illustrated in FIG. 1 as a triac 19. As can be seen, the sensing and trigger means 11 is also fed from the input.

Figure 2:
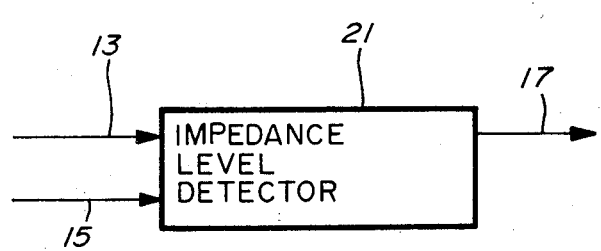
FIG. 2 is a block diagram of the sensing and trigger function of FIG. 1.

Turning now to FIG. 2, the sensing and trigger means 11 will comprise an impedance level detector 21. The impedance level detector 21 can comprise such well known means as an A.C. impedance bridge. In any case, it will measure the conductivity between leads 13 and 15 or, more specifically, between the center and outer conductors of the lithotrite to which leads 13 and 15 are respectively connected.

As seen in FIG. 1, lead 17 of the sensing and trigger means 11 is fed to a processor 51 which is preferably a microprocessor. The microprocessor will receive the conductivity level sensed by the means 11 and determine whether it falls within a conductivity window, that is, within predetermined conductivity levels. If it falls within the window, then the processor will provide a triggering signal to triac 19 via contact $C_b$ of switch S3 and lead 18. At the same time, it will provide a signal to EMI filter 1 to set the level of the primary voltage as a function of the conductivity level.

The processor will also provide an output to a display circuit drive 53 which can then display warning conditions as follows:

(A) Shorted Electrode
(B) Tissue Contact
(C) Normal Operating Range
(D) Low Ionic Concentration
(E) No Electrode or Improper Cable Configuration.

The warning conditions will provide information to the operators for use in the manual mode as will be discussed below.

An additional warning condition presented to the operator will be based on predicted electrode life. The microprocessor 51 can keep track of the voltage and time that an individual electrode is exposed to. When the voltage time product reaches a predetermined value, a warning may be presented to the operator informing him of impending electrode failure. A reset switch would be provided so that the operator can reset the warning function when the new electrode is connected to the machine.

Switch S3 provides a manual override and includes contacts $C_a$ and $C_b$. Obviously, two separate switches could be provided.

In operation, the instrument works as follows:

As is well known in the art, the lithotrite is first inserted in the patient close to the calculi or stones which have to be disintegrated, and the free end of the lithotrite will be in the liquid medium surrounding the calculi. The lithotrite will be positioned adjacent to the calculi by means well known in the art.

The input is connected to a source of AC such as 120 volts AC and is fed, through the fuse F1 and through the switch S1, to the EMI filter 1. When switch S1 is turned on, then power will be available at the transformer T1, at the relay ON/OFF lamp circuit L2, and at the sensing and trigger means 11.

The availability of this power is indicated by the illumination of lamp L1.

To set the instrument in operation, foot pedal S2 is depressed. When the foot pedal S2 is depressed, power is provided to the relay Y to actuate the relay so that the contacts SC1, SC2, SC3 and SC4 are closed. The depression of the foot pedal is indicated by illumination of the lamp L2.

As the triac 19 is biased to be in its non-conductive condition, power will not be provided to the transformer t1, so that the capacitor C1 and C2 will not charge up at this time. However, power will be provided to the sensing and trigger means 11.

As the sensing and trigger means is now operational, the conductivity of the liquid medium surrounding the calculi or stones to be disintegrated is measured in the impedance level detector, and the measurement level is examined in the processor to determine if it is within the predetermined window or set of conductivity levels. It is noted in this regard that, when the lithotrite is abutting or close to human tissue, then its conductivity is far different from the conductivity of the liquid medium surrounding the calculi. Accordingly, when the lithotrite is in such a dangerous position, then the conductivity level which is measured will not fall within this window.

It is also noted in this regard that the primary voltage can be adjusted as a function of level of conductivity to optimize spark discharge within the predetermined window.

If there is a low ionic concentration, then it is possible to alter the conductivity of the surrounding liquid medium. For example, a saline solution can be inserted into the liquid medium to change its conductivity. As is well known in the art, the saline solution would be so inserted via a hose which would also be carried in the cable 29.

When the conductivity level is within the limits set by the reference signal generator, lead 18 will carry a triggering pulse to the control terminal of the triac 19 to turn the triac on. When the triac is turned on, then adjusted power will be supplied to the primary of the transformer. Accordingly, the secondary of the transformer will drive the pulse forming network to charge the capacitor C1 and C2. When the capacitors have been charged to the appropriate level, the switching arrangement 5 will be closed to thereby cause a spark discharge between the inner and outer electrodes of the lithotrite, and the impact of the spark discharge will, as is well known in the art, disintegrate the calculi or stones.

A manual override switch S3, having contacts $C_a$ and $C_b$, may be provided to take the triac out of the circuit. When S3-$C_a$ is closed and S3-$C_b$ is open, then the instrument will operate regardless of the conductivity level of the liquid medium surrounding the calculi. That is, switch S3-$C_a$ will short out the triac so that power will be presented to the primary regardless of the level of conductivity. At the same time, the output of the processor 51 will be disconnected from the triac by opening contact $C_b$ of Switch S3.

In an alternative, and preferred embodiment, manual override is effected by way of manual manipulation of the processor 51 by means of, for example, a control mechanism 52. The processor is adjusted to provide the sensing and trigger means 11 with an apparent or artificial conductivity level signal. The level of this artificial signal can be set so that it falls within the limits of the reference signal generator, whereupon the triac will remain conductive regardless of the actual conductivity level.

It can be seen from the above description that, with the improvement to the instrument, the instrument will be prevented from operating, i.e., providing a spark discharge, when the conductivity level measured at the free end of the lithotrite indicates that the free end of the lithotrite is adjacent to human tissue. Accordingly, the patient will not be hurt because of discharge when the lithotrite is in this dangerous position. The above action takes place when the instrument is in the automatic mode, i.e., contact $C_a$ of switch S3 is open and contact $C_b$ of switch S3 is closed. In the manual mode, with the contacts in the opposite direction, there will still be indications, as above-mentioned, of tissue contact so that the operator can take appropriate precautions.

In addition, in the automatic mode, the primary voltage will be adjusted as a function of the conductivity. The adjustment will take place by the action of the processor 51.

The primary voltage can also be adjusted manually when the instrument is in the manual mode.

Although a particular embodiment has been above-described, this was for the purpose of illustrating, but not limiting, the invention. Various modifications, which will come readily to the mind of one skilled in the art, are within the scope of the invention as defined in the appended claims.

We claim:

1. In an instrument for attacking calculi of a patient in a liquid medium surrounding the calculi, said instrument including a lithotrite having a free, discharge, end, said free, discharge, end being disposed, in operation, adjacent the calculi being attacked, the improvement comprising:

means for detecting if said discharge end is adjacent to tissue of said patient;

said means for detecting being disposed at said discharge end whereby said means for detecting is disposed, in operation, adjacent said calculi being attacked; and means for preventing operation of said instrument when said discharge end is adjacent said tissue.

2. The improvement of claim 1 wherein said means for detecting comprises an impedance level detector;

means for connecting an input of said impedance level detector to the center and outer conductors respectively of said lithotrite;

whereby, when said lithotrite is in said liquid medium, said impedance level detector detects the conductivity of the liquid medium.

3. The improvement of claim 2 wherein said means for detecting determines whether the measured conductivity falls within predetermined levels of conductivity; and means for actuating said instrument when the measured conductivity falls within the predetermined levels.

4. The improvement as defined in claim 3 wherein said means for detecting comprises microprocessor means.

5. The improvement as defined in claim 4 wherein said instrument includes a power input means and a transformer, the primary of said transformer being connected to said power input means;

electronic switch means in circuit with said primary, said electronic switch means being normally biased in its off, or non-conductive, condition, said electronic switch including a control terminal;

said means for determining comprising an output trigger terminal, said trigger terminal being connected to the control terminal of said electronic switch;

whereby, when said measured conductivity falls within said predetermined levels, said means for determining provides a triggering pulse on said triggering terminal to turn said electronic switch on.

6. The improvement as defined in claim 5 wherein said electronic switch comprises a triac.

7. The improvement as defined in claim 6 and including manual override switch in parallel with said electronic switch to short-out said electronic switch when said manual override switch is closed.

8. The improvement as defined in claim 6 and including manual override means for maintaining said triac in a continuous conductive condition, comprising, manual means for controlling said microprocessor means to provide an artificial conductivity level which falls within said predetermined levels whereby said triac remains in a continuously conductive state regardless of the conductivity of the liquid medium.

9. In an instrument for attacking calculi of a patient in a liquid medium surrounding the calculi, said instrument including a lithotrite having a free, discharge, end, said free, discharge, end being disposed, in operation, adjacent the calculi being attacked, the improvement comprising:

means for measuring the conductivity of the liquid medium said means for measuring being disposed in the discharge end of said instrument; and means for preventing operation of said instrument when said conductivity falls outside of predetermined limits;

whereby, when said instrument is in operation, said means for measuring is adjacent said calculi being attacked.

* * * * *